United States Patent
Okuda et al.

(10) Patent No.: US 10,106,523 B2
(45) Date of Patent: Oct. 23, 2018

(54) AMIDE COMPOUND

(71) Applicant: ASTELLAS PHARMA INC., Chuo-ku (JP)

(72) Inventors: Takao Okuda, Tokyo (JP); Eisuke Nozawa, Tokyo (JP); Tohru Ugawa, Tokyo (JP); Ryo Mizoguchi, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 29 days.

(21) Appl. No.: 15/127,574

(22) PCT Filed: Mar. 25, 2015

(86) PCT No.: PCT/JP2015/059026
§ 371 (c)(1),
(2) Date: Sep. 20, 2016

(87) PCT Pub. No.: WO2015/147020
PCT Pub. Date: Oct. 1, 2015

(65) Prior Publication Data
US 2018/0030030 A1    Feb. 1, 2018

(30) Foreign Application Priority Data
Mar. 26, 2014 (JP) ................. 2014-064590

(51) Int. Cl.
*C07D 401/06* (2006.01)
*A61K 31/4725* (2006.01)

(52) U.S. Cl.
CPC ........ *C07D 401/06* (2013.01); *A61K 31/4725* (2013.01)

(58) Field of Classification Search
CPC ..................................... C07D 401/06
See application file for complete search history.

(56) References Cited

U.S. PATENT DOCUMENTS

| | | |
|---|---|---|
| 2009/0247596 A1 | 10/2009 | Blouin et al. |
| 2011/0028463 A1 | 2/2011 | Nozawa et al. |
| 2011/0144153 A1 | 6/2011 | Nozawa et al. |
| 2013/0237578 A1 | 9/2013 | Spyvee et al. |
| 2014/0155452 A1 | 6/2014 | Spyvee et al. |

FOREIGN PATENT DOCUMENTS

| | | |
|---|---|---|
| WO | 2008/017164 A2 | 2/2008 |
| WO | 2009/005076 A1 | 1/2009 |
| WO | 2009/139373 A1 | 11/2009 |
| WO | 2012/039972 A1 | 3/2012 |
| WO | 2012/103071 A2 | 8/2012 |

OTHER PUBLICATIONS

International Search Report dated Jun. 23, 2015 in PCT/JP2015/059026 filed Mar. 25, 2015.

*Primary Examiner* — Brian E McDowell
(74) *Attorney, Agent, or Firm* — Oblon, McClelland, Maier & Neustadt, L.L.P.

(57) ABSTRACT

A compound which is useful as an active ingredient of a pharmaceutical composition, for example, a pharmaceutical composition for treating chronic renal failure and/or diabetic nephropathy is provided.

9 Claims, No Drawings

AMIDE COMPOUND

TECHNICAL FIELD

The present invention relates to 4-[(1S)-1-({[4-bromo-1-(isoquinolin-3-ylmethyl)-3-methyl-1H-pyrazol-5-yl]carbonyl}amino)ethyl]benzoic acid (hereinafter referred to as "Compound A" in some cases) or a salt thereof, which is useful as an active ingredient of a pharmaceutical composition, for example, a pharmaceutical composition for treating chronic renal failure and/or diabetic nephropathy.

BACKGROUND ART

Prostaglandin E2 (hereinafter referred to as "PGE2") is known as one of the metabolites in an arachidonic acid cascade. PGE2 exhibits various physiological activities and is involved in a pain inducing and increasing action, a pro-inflammatory action, an anti-inflammatory action, a uterine contractile action, a digestive peristalsis promoting action, an awaking action, a gastric acid secretion inhibiting action, a hypotensive action, a platelet aggregation inhibition action, a bone resorption-promoting action, an angiogenic action, and the like.

There exist four subtypes, EP1, EP2, EP3, and EP4, for PGE2 receptors, which have a wide distribution in various tissues. The activation of the EP1 receptor causes the increase in intracellular $Ca^{2+}$. The activation of the EP3 receptor causes the increase in intracellular $Ca^{2+}$ and causes the inhibition of adenylate cyclase, and thus decreases the intracellular cAMP level. The activation of the EP2 and EP4 receptors causes the activation of adenylate cyclase, and thus increases the intracellular cAMP level. In particular, it is believed that the EP4 receptor is related to relaxation of smooth muscles, promotion or inhibition of an inflammatory reaction, lymphocyte differentiation, hypertrophy or proliferation of mesangial cells, secretion of gastrointestinal mucus, and the like (Pharmacology & Therapeutics 2013, 138:485-502; Pharmacological Reviews 2013, 65:1010-1052; and American Journal of Physiology Renal Physiology 2004, 287, F673-F681).

An inhibitor of a PGE2 receptor, that is, an EP receptor antagonist has a binding activity to the EP receptor and inhibits the action by an EP receptor of PGE2. Accordingly, an EP receptor antagonist is expected to be an agent for treating diseases caused by PGE2. Among these, the EP4 receptor antagonist is expected to be a drug for treating EP4-related diseases, for example, renal disease, inflammatory diseases, and various pains, in human and animals (Journal of American Society Nephrology 2010, 21:1678-1690; Proceedings of the National Academy of Sciences, 2010, 107:12233-12238; and The Journal of Pharmacology and Experimental Therapeutics 2008, 325:425-434). In addition, the antagonist selective to the EP4 receptor is preferred from the viewpoint that it can avoid the side-effects based on the antagonism of other EP1, EP2, and EP3 (Physiological Reviews 1999, 79:1193-1226; and Annual Reviews Physiology 2001, 63:579-605).

In Patent Document 1, a compound represented by the following formula (B) is reported as an EP4 receptor antagonist.

[Chem. 1]

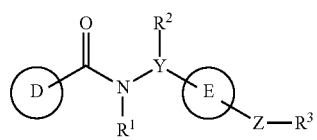

(B)

(In the formula, the ring D represents a group of the following formula (III), or the like, and in the following formula, the ring $D^1$ represents a monocyclic or bicyclic nitrogen-containing hetero ring which may be substituted with phenyl, $R^{41}$ represents —$X^2$—$B^4$, $X^2$ represents a $C_{1-6}$ alkylene or the like, and $B^4$ represents aryl, a hetero ring, or the like, each of which may be substituted with the same or different 1 to 5 groups selected from $R^4$. For the other symbols, refer to this Patent Document.)

[Chem. 2]

(III)

In Example 205 of this Patent Document, the following Example compound is disclosed, and this Example compound is disclosed as a specific compound in which the ring $D^1$ is pyrazole.

[Chem. 3]

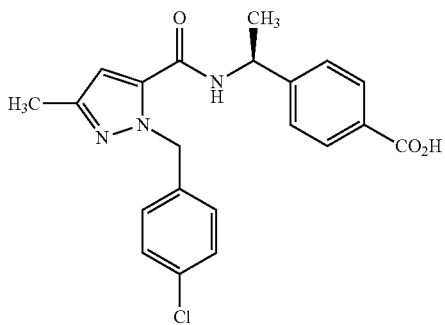

In Patent Document 2, a compound represented by the following formula (C) is reported as the EP4 receptor antagonist.

[Chem. 4]

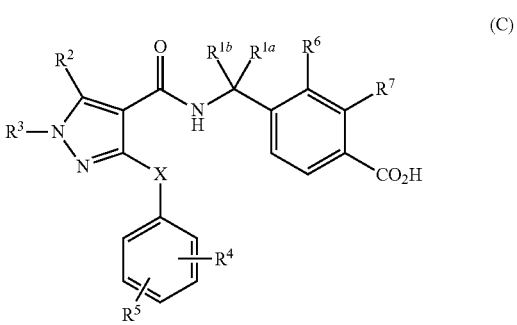

(C)

(In the formula, $R^2$ represents methyl, fluoromethyl, or the like, and $R^4$ represents fluoromethyl, methoxy, or the like. For the other symbols in the formula, refer to this Patent Document.)

In Patent Document 3, a compound represented by the following formula (D) is reported as an EP4 receptor antagonist.

[Chem. 5]

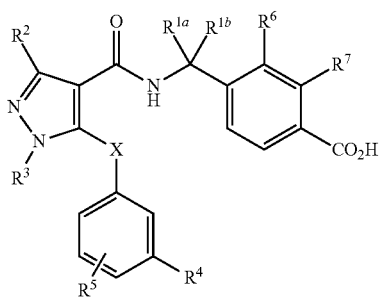

(In the formula, $R^2$ represents methyl, fluoromethyl (for example, monofluoromethyl, difluoromethyl, and trifluoromethyl), or the like, and $R^4$ represents fluoromethyl, methoxy, or the like. For the other symbols, refer to this Patent Document.)

In Patent Document 4, a compound represented by the following formula (E) is reported as an EP4 receptor ligand.

[Chem. 6]

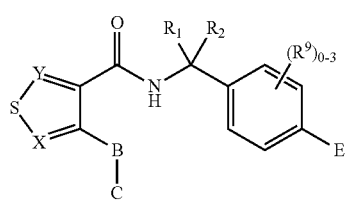

(For the symbols in the formula, refer to this Patent Document.)

In Patent Document 5, a compound represented by the following formula (F) is reported as an EP4 receptor antagonist.

[Chem. 7]

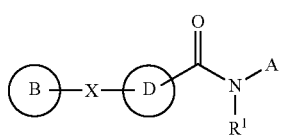

(In the formula, the ring B and the ring D are the same as or different from each other, and represent aryl which may be substituted or a hetero ring which may be substituted, X represents a single bond, $-R^{00}-$, or the like, $R^{00}$ represents lower alkylene, and $R^1$ represents H or the like. A represents a group of the following formula (II), or the like, and in the following formula, Y represents CH or the like, $R^2$ represents $R^0$ or the like, $R^0$ represents lower alkyl, Z represents a single bond or the like, and $R^3$ represents —COOH or the like. For the other symbols, refer to this Patent Document.)

[Chem. 8]

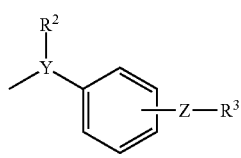

In this Patent Document, there is no disclosure of a specific compound in which the ring D is pyrazole.

In Patent Documents 1 to 5, the structures of the compounds specifically disclosed in Examples are different from that of Compound A.

RELATED ART

Patent Documents

[Patent Document 1] WO 2009/139373
[Patent Document 2] WO 2012/103071
[Patent Document 3] WO 2012/039972
[Patent Document 4] WO 2008/017164
[Patent Document 5] WO 2009/005076

DISCLOSURE OF INVENTION

Problems to be Solved by the Invention

A compound which is useful as an active ingredient of a pharmaceutical composition, for example, a pharmaceutical composition for treating chronic renal failure and/or diabetic nephropathy is provided.

Means for Solving the Problems

The present inventors have conducted extensive studies on a compound having an EP4 receptor antagonistic action and have found that 4-[(1S)-1-({[4-bromo-1-(isoquinolin-3-ylmethyl)-3-methyl-1H-pyrazol-5-yl]carbonyl}amino) ethyl]benzoic acid (Compound A), represented by the formula (I), or a salt thereof exhibits an excellent EP4 receptor antagonistic action, thereby completing the present invention.

[Chem. 9]

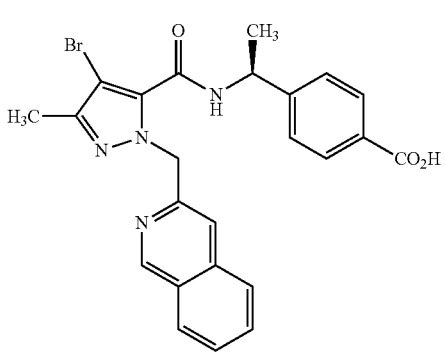

That is, the present invention relates to Compound A or a salt thereof, and a pharmaceutical composition comprising Compound A or a salt thereof and a pharmaceutically acceptable excipient.

Furthermore, the present invention relates to a pharmaceutical composition for preventing or treating chronic renal failure and/or diabetic nephropathy, comprising Compound A or a salt thereof, and a pharmaceutically acceptable excipient. Further, this pharmaceutical composition includes an agent for preventing or treating chronic renal failure and/or diabetic nephropathy, comprising Compound A or a salt thereof, and a pharmaceutically acceptable excipient.

Furthermore, the present invention relates to use of Compound A or a salt thereof for the manufacture of a pharmaceutical composition for preventing or treating chronic renal failure and/or diabetic nephropathy; use of Compound A or a salt thereof for preventing or treating chronic renal failure and/or diabetic nephropathy; Compound A or a salt thereof for preventing or treating chronic renal failure and/or diabetic nephropathy; and a method for preventing or treating chronic renal failure and/or diabetic nephropathy, comprising administering an effective amount of Compound A or a salt thereof to a subject. Incidentally, the "subject" is a human or a non-human animal in need of the prevention or treatment, and in an embodiment, a human in need of the prevention or treatment.

Effects of the Invention

Compound A or a salt thereof has an EP4 receptor antagonistic action and can be used as an active ingredient of a pharmaceutical composition for preventing and/or treating chronic renal failure and/or diabetic nephropathy.

EMBODIMENTS FOR CARRYING OUT THE INVENTION

An embodiment of Compound A or a salt thereof of the present invention is shown below. Further, in the present specification, in a case where Compound A is simply described, this refers to Compound A as a free form in which a salt is not formed.

(1) Compound A or a salt thereof.
(1-1) Compound A.
(1-2) A methanesulfonate of Compound A.
(2) A crystal of Compound A or a salt thereof described in (1).
(3) A crystal of Compound A described in (1-1).
(3-1) A crystal of Compound A described in (3), in which the onset temperature of an endothermic peak in differential scanning calorimetry (DSC analysis) is around 253° C.
(3-2) A crystal of Compound A described in (3), which exhibits peaks at 2θ (°)=around 5.7, around 7.9, around 11.5, around 13.1, and around 17.9 in powder X-ray diffraction using Cu as a tube.
(3-3) A crystal of Compound A described in (3), which exhibits peaks at 2θ (°)=around 5.7, around 7.9, around 8.3, around 8.9, around 9.2, around 11.5, around 12.5, around 13.1, around 15.8, around 16.3, around 16.7, around 17.2, around 17.9, around 18.5, and around 19.5 in powder X-ray diffraction using Cu as a tube.
(3-4) A crystal of Compound A described in (3), which has an onset temperature of an endothermic peak in DSC analysis of around 253° C., and exhibits peaks at 2θ (°)=around 5.7, around 7.9, around 11.5, around 13.1, and around 17.9 in powder X-ray diffraction using Cu as a tube.
(3-5) A crystal of Compound A described in (3), which has an onset temperature of an endothermic peak in DSC analysis of around 253° C., and exhibits peaks at 2θ (°)=around 5.7, around 7.9, around 8.3, around 8.9, around 9.2, around 11.5, around 12.5, around 13.1, around 15.8, around 16.3, around 16.7, around 17.2, around 17.9, around 18.5, and around 19.5 in powder X-ray diffraction using Cu as a tube.
(4) A crystal of a methanesulfonate of Compound A described in (1-2).
(4-1) The crystal of a methanesulfonate of Compound A described in (4), which has an onset temperature of an endothermic peak in DSC analysis of around 192° C.
(4-2) The crystal of a methanesulfonate of Compound A described in (4), which exhibits peaks at 2θ (°)=around 4.7, around 9.5, around 12.0, around 13.2, around 13.7, around 15.3, around 18.8, around 20.3, around 20.9, and around 22.8 in powder X-ray diffraction using Cu as a tube.
(4-3) The crystal of a methanesulfonate of Compound A described in (4), which has an onset temperature of an endothermic peak in DSC analysis of around 192° C., and exhibits peaks at 2θ (°)=around 4.7, around 9.5, around 12.0, around 13.2, around 13.7, around 15.3, around 18.8, around 20.3, around 20.9, and around 22.8 in powder X-ray diffraction using Cu as a tube.
(5-1) A pharmaceutical composition comprising the compound described in any one of (1) to (1-2), and a pharmaceutically acceptable excipient.
(5-2) A pharmaceutical composition comprising the crystal described in any one of (2) to (4-3), and a pharmaceutically acceptable excipient.
(5-3) A pharmaceutical composition for preventing or treating chronic renal failure and/or diabetic nephropathy, comprising the compound described in any one of (1) to (1-2), and a pharmaceutically acceptable excipient.
(5-4) A pharmaceutical composition for preventing or treating chronic renal failure and/or diabetic nephropathy, comprising the crystal described in any one of (2) to (4-3), and a pharmaceutically acceptable excipient.
(6-1) Use of the compound described in any one of (1) to (1-2) for the manufacture of a pharmaceutical composition for preventing or treating chronic renal failure and/or diabetic nephropathy.
(6-2) Use of the crystal described in any one of (2) to (4-3) for the manufacture of a pharmaceutical composition for preventing or treating chronic renal failure and/or diabetic nephropathy.
(7-1) The compound described in any one of (1) to (1-2) for preventing or treating chronic renal failure and/or diabetic nephropathy.
(7-2) The crystal described in any one of (2) to (4-3) for preventing or treating chronic renal failure and/or diabetic nephropathy.
(8-1) Use of the compound described in any one of (1) to (1-2) for preventing or treating chronic renal failure and/or diabetic nephropathy.
(8-2) Use of the crystal described in any one of (2) to (4-3) for preventing or treating chronic renal failure and/or diabetic nephropathy.
(9-1) A method for preventing or treating chronic renal failure and/or diabetic nephropathy, comprising administering an effective amount of the compound described in any one of (1) to (1-2) to a subject.
(9-2) A method for preventing or treating chronic renal failure and/or diabetic nephropathy, comprising administering an effective amount of the crystal described in any one of (2) to (4-3) to a subject.

Additionally, the present invention further includes a pharmaceutically acceptable prodrug of Compound A or a salt thereof. The pharmaceutically acceptable prodrug refers to a compound having a group which can be converted into a carboxyl group by solvolysis or under physiological conditions. Examples of the group for forming a prodrug include those described in Prog. Med., 5, 2157-2161 (1985) or "Pharmaceutical Research and Development" (Hirokawa Publishing Company, 1990), vol. 7, Drug Design, 163-198.

In the present invention, a salt of Compound A is a pharmaceutically acceptable salt, and Compound A may form an acid addition salt or a salt with a base in some cases. Specific examples of the salt include acid addition salts with inorganic acids such as hydrochloric acid, hydrobromic acid, hydroiodic acid, sulfuric acid, nitric acid, and phosphoric acid, or with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditolyl tartaric acid, citric acid, methanesulfonic acid, ethanesulfonic acid, benzenesulfonic acid, p-toluenesulfonic acid, aspartic acid, and glutamic acid, and salts with inorganic bases such as sodium, potassium, magnesium, calcium, and aluminum, or with organic bases such as methylamine, ethylamine, ethanolamine, lysine, and ornithine, salts with various amino acids such as acetyl leucine, or with derivatives of amino acids, and ammonium salts.

Moreover, the present invention further includes various hydrates or solvates, and polymorphism of Compound A or a salt thereof. In addition, the present invention also includes Compound A or a salt thereof, labeled with various radioactive or non-radioactive isotopes.

In the present specification, the term "around" included in the description of the diffraction angle (2θ (°)) in powder X-ray diffraction pattern and the onset temperature (° C.) of an endothermic peak in DSC analysis has a meaning including a usually acceptable error range in this data measurement method, and typically means an onset value of the diffraction angle and the endothermic peak. The error range of the diffraction angle (2θ (°)) in powder X-ray diffraction is, in one embodiment, ±0.2°, and in another embodiment, ±0.1°. The error range of the onset temperature of an endothermic peak in DSC analysis (° C.) is, in one embodiment, ±2° C., and in another embodiment, ±1° C.

In addition, with the powder X-ray diffraction pattern, crystal lattice spacing and overall patterns are important for identification of crystals in terms of the properties of the data, and the diffraction angle and the diffraction strength may vary slightly depending on the direction of crystal growth, the particle size, and the measurement conditions.

(Preparation Method)

Compound A or a salt thereof can be prepared by applying various known synthesis methods, using the characteristics based on their basic structures or the kinds of the substituents. At this time, depending on the types of the functional groups, it is in some cases effective from the viewpoint of the preparation techniques to substitute the functional group with an appropriate protecting group (a group which is capable of being easily converted into the functional group), during the steps from starting materials to intermediates. Examples of the protecting group include the protective groups as described in "Greene's Protective Groups in Organic Synthesis (4$^{th}$ edition, 2006)", P. G. M. Wuts and T. W. Greene, and the like, which may be appropriately selected and used depending on the reaction conditions. In these methods, a desired compound can be obtained by introducing the protecting group to carry out the reaction, and then, if desired, removing the protecting group.

Additionally, the prodrug of Compound A can be prepared by introducing a specific group during the steps from starting materials to intermediates, in the same manner as for the above protecting groups, or by carrying out an additional reaction using the obtained Compound A. The reaction can be carried out by applying a method known by a person skilled in the art, such as general esterification, amidation, dehydration, and the like.

Hereinbelow, typical preparation methods of Compound A will be described. Each of the preparation processes can also be carried out with reference to the documents appended to the description herein. In this connection, the preparation method of the present invention is not limited to the examples as shown below. In addition, unless specifically described otherwise, in the case where the symbols in the structural formulae in the present preparation method are also used in other structural formulae, the same symbols denote the same meanings.

(Preparation Process 1)

[Chem. 10]

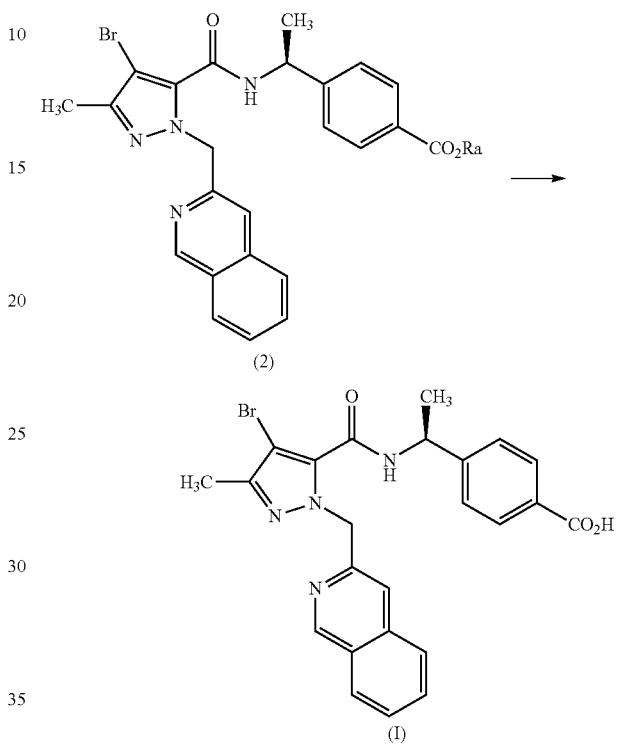

(In the formula, Ra is a linear or branched alkyl having 1 to 6 carbon atoms, for example, methyl, ethyl, or the like.)

Compound A represented by the formula (I) can be prepared by the hydrolysis of a compound represented by the general formula (2). Here, the hydrolysis reaction can be carried out with reference to "Greene's Protective Groups in Organic Synthesis (4$^{th}$ edition, 2006)" above.

(Starting Material Synthesis)

Starting Material Preparation Process 1

[Chem. 11]

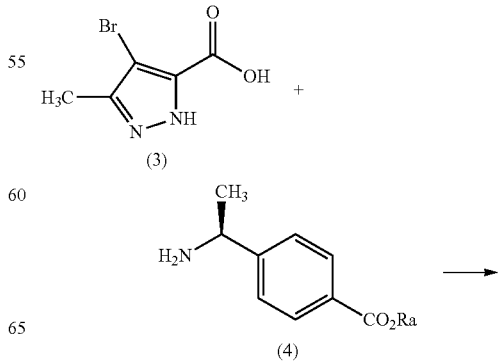

-continued

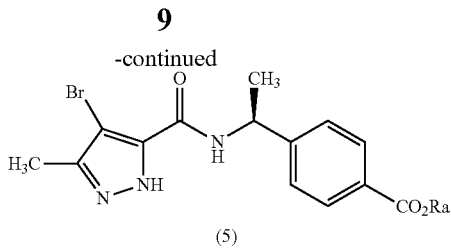

(5)

(I)

A starting compound (5) can be prepared by an amidation reaction of a compound (3) and a compound (4).

The reaction is carried out using an equivalent amount of the compound (3) and the compound (4) or an excess amount of either thereof, by stirring the mixture in a range from under cooling to under heating, preferably at −20° C. to 60° C., usually for 0.1 hour to 5 days, in a solvent which is inert to the reaction, in the presence of a condensing agent. Here, the solvent is not particularly limited, but examples thereof include aromatic hydrocarbons such as benzene, toluene, xylene and the like, halogenated hydrocarbons such as dichloromethane (DCM), 1,2-dichloroethane (DCE), chloroform and the like, ethers such as diethyl ether, tetrahydrofuran (THF), dioxane, dimethoxyethane (DME) and the like, N,N-dimethylformamide (DMF), dimethylsulfoxide (DMSO), ethyl acetate, acetonitrile, or water, or a mixture thereof. As the condensing agent, 1-[bis(dimethylamino)methylene]-1H-1,2,3-triazolo [4,5-b]pyridin-1-ium-3-oxide hexafluorophosphate (HATU), 1-(3-dimethylaminopropyl)-3-ethylcarbodiimide hydrochloride, 1-(3-dimethylaminopropyl)-3-ethylcarbodiimide, dicyclohexylcarbodiimide (DCC), 1,1'-carbonyldiimidazole (CDI), diphenylphosphoric azide, phosphorus oxychloride, a condensing agent-carrying polystyrene resin, for example, PS-carbodiimide (Argonaut Technologies, Inc., USA), or the like may be preferably used in some cases, but not limited thereto. Further, it may be preferable in some cases for the reaction to use an additive such as, for example, 1-hydroxybenzotriazole (HOBt) or the like, and it may be advantageous in some cases for the smooth progress of the reaction to carry out the reaction in the presence of, for example, an organic base such as triethylamine (TEA), N,N-diisopropylethylamine (DIPEA), N-methylmorpholine (NMM) and the like, or an inorganic base such as potassium carbonate, sodium carbonate, potassium hydroxide and the like. Also, it is preferable to use an isocyanate-carrying polystyrene resin, for example, PS-Isocyanate (Argonaut Technologies, Inc., USA) and the like, in order to remove excess amine after completion of the reaction. In addition, a quaternary ammonium salt-carrying polystyrene resin, for example, MP-Carbonate (Argonaut Technologies, Inc., USA) and the like can be used, in order to remove excess carboxylic acid and the aforementioned additives, and the like, after completion of the reaction.

Furthermore, a method, in which the compound (3) is induced to a reactive derivative thereof, and then the reactive derivative is reacted with the compound (4), can also be used. Here, examples of the reactive derivative of the compound (3) include acid halides obtained by the reaction with a halogenating agent such as phosphorus oxychloride, thionyl chloride and the like, mixed acid anhydrides obtained by the reaction with isobutyl chloroformate or the like, active esters obtained by condensation with HOBt or the like, and others. The reaction of these reactive derivatives with the compound (4) can be carried out in a range from under cooling to under heating, preferably at −20° C. to 60° C., in a solvent which is inert to the reaction, such as halogenated hydrocarbons, aromatic hydrocarbons, and ethers.

Starting Material Preparation Process 2

[Chem. 12]

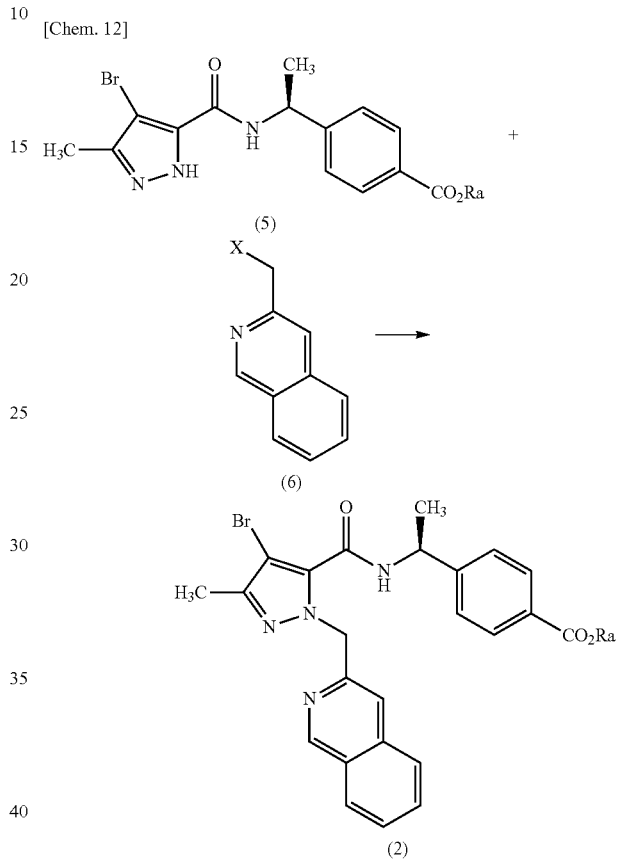

(In the formula, X represents a leaving group.)

The starting compound (2) can be prepared by an alkylation reaction of a compound (5) and a compound (6).

Specific examples of the leaving group represented by X include halogen, methanesulfonyloxy, p-toluenesulfonyloxy, trifluoromethanesulfonyloxy groups and the like.

This reaction is carried out using an equivalent amount of the compound (5) and the compound (6) or an excess amount of either thereof, by stirring the mixture in a range from under cooling to under heating with reflux, preferably at 0° C. to 80° C., in a solvent which is inert to the reaction or without a solvent, usually for 0.1 hours to 10 days. Examples of the solvent as used herein are not particularly limited, but include aromatic hydrocarbons such as benzene, toluene, xylene and the like, ethers such as diethyl ether, THF, dioxane, DME and the like, halogenated hydrocarbons such as DCM, DCE, chloroform and the like, DMF, DMSO, 1-methyl-2-pyrrolidone, dimethylacetamide, acetone, ethyl acetate, acetonitrile, and a mixture thereof. It may be advantageous in some cases for the smooth progress of the reaction to carry out the reaction in the presence of an organic base such as TEA, DIPEA, NMM and the like, or an inorganic base such as potassium tert-butoxide, cesium carbonate, potassium carbonate, sodium carbonate, potassium hydroxide and the like.

Compound A is isolated and purified as its free compound, a salt thereof, a hydrate, a solvate, or a polymorph. The salt of Compound A can be prepared by carrying out a conventional salt formation reaction.

Isolation and purification can be carried out by employing general chemical operations such as extraction, fractional crystallization, various types of fractional chromatography, and the like.

For example, the optical isomers can be obtained by means of general optical resolution methods for racemic compounds (for example, by fractional crystallization introducing the compound into diastereomer salts with optically active bases or acids, chromatography using a chiral column or the like, and others), or can also be prepared from a suitable optically active starting compound.

The pharmacological activity of Compound A was confirmed by the following tests.

Test Example 1: Evaluation Test of Rat EP4 Receptor Affinity

Construction of Rat EP4 Receptor Expressing Vector:
A rat EP4 receptor gene (GenBank accession No.: NM_032076.1) was transfected into an expression vector pcDNA3.1-V5-His-TOPO (Invitrogen Inc.).

Transient Expression of Rat EP4 Receptor:
The expression vector of a rat EP4 receptor was transfected into an HEK-293 cell (ATCC No.: CRL-1573). The transfection was carried out according to an appended instruction, using Lipofectoamine (registered trademark) 2000 reagent (Invitrogen Inc.). After the transfection, the cells were cultured in an α-MEM culture medium for 20 to 24 hours.

Preparation of Membrane Fraction:
The culture medium was removed by aspiration, 10 mL of cooled phosphate buffered saline (PBS) was added thereto per 15 cm dish, and the cells were scraped using a cell scraper (Sumitomo Bakelite). The cells were collected, centrifuged (250×g, 4° C., 5 min), and then suspended in 6 mL of cooled 20 mmol/L Tris-HCl (pH 7.4; Nakalai Tesque Inc., containing 5 mmol/L ethylenediamine tetraacetic acid (EDTA, Nakalai Tesque Inc.)) per dish. The resultant was homogenized using Polytron (registered trademark) and the homogenate was centrifuged (69,000×g, 20 min, 4° C.). The obtained precipitate was resuspended in cooled 20 mmol/L Tris-HCl and homogenized again using a Polytron, and the homogenate was centrifuged (69,000×g, 20 min, 4° C.). The obtained precipitate was suspended in 50 mmol/L HEPES-NaOH (Dojindo Laboratories) (pH 7.5) at 1 mL per dish, then homogenized, and cryopreserved at −80° C. as a membrane fraction. At this time, a part thereof was used for the measurement of the protein concentration. Measurement of the protein concentration was carried out in duplicate, using a Bio-Rad Protein assay kit (Bio-Rad Laboratories) in accordance with the appended standard protocol.

Binding Assay:
[$^3$H]PGE2 and a cell membrane fraction were diluted with an assay buffer (50 mmol/L HEPES-NaOH, 10 mmol/L MgCl$_2$, pH 7.5), and the test compound and unlabeled PGE2 (Cayman) were diluted with DMSO and the assay buffer. The composition of the reaction liquid (200 μL) was set to be as follows: 50 μL of 50 mmol/L HEPES-NaOH (pH 7.5), 10 mmol/L MgCl$_2$, 0.3 nmol/L [$^3$H]PGE2 (Perkin Elmer), 100 μL of a rat EP4 cell membrane fraction (200 μg protein/mL), and 50 μL of a test compound (final concentrations of 0.1, 0.3, 1, 3, 10, 30, and 100 nmol/L). For the measurement of the non-specific binding, the unlabeled PGE2 (Cayman) was added to a final concentration of 1 μmol/L. The final concentration of DMSO was set to 1%. The reaction liquid was incubated in a 96-well microplate (Sumitomo Bakelite) at room temperature for 1 hour. The reaction liquid was filtered with a filter paper UniFilter-96GF/B (Perkin Elmer), using a FilterMate harvester (Perkin Elmer). The filter paper after filtration was washed three times with 300 μL/well of a cooling assay buffer, and then dried in a dryer overnight. 50 μL/well of a liquid scintillator, MicroScint20 (Perkin Elmer), was added thereto. The radioactivity was measured using a TopCount (Perkin Elmer). The measurement was carried out once in duplicate in all cases. The specific binding amount was determined by subtracting the non-specific binding amount from the total binding amount. The Ki value was calculated according to a standard method.

As a result of the evaluation, it was found that the Ki value of Compound A with respect to the rat EP4 receptor was 0.874 nmol/L. Further, the Ki value of the compound of Example 205 in Patent Document 1 with respect to the rat EP4 receptor was 140 nmol/L.

Test Example 2: Evaluation Test of Human EP4 Receptor Affinity

Binding Assay:
[$^3$H]PGE2 and a human EP4 cell membrane fraction (Chemicon) were diluted with an assay buffer (50 mmol/L HEPES-NaOH, 5 mmol/L MgCl$_2$, 1 mmol/L CaCl$_2$ (pH 7.4), 0.5% bovine serum albumin (BSA)), and the test compound and unlabeled PGE2 (Sigma) were diluted with DMSO and the assay buffer. The composition of the reaction liquid (250 μL) was set to be as follows: 175 μL of an assay buffer containing [$^3$H]PGE2 (final concentration of 2.9 nmol/L), 50 μL of a membrane fraction (Chemicon, 40 μg protein/mL), and 25 μL of a test compound (final concentrations of 0.1, 1, 10, 100, and 1000 nmol/L). For the measurement of the non-specific binding, the unlabeled PGE2 was added to a final concentration of 10 μmol/L. The final concentration of DMSO was set to 1%. The reaction liquid was incubated at 25° C. for 60 minutes. The reaction liquid was filtered with a GF/C filter paper (Whatman), using a cell harvester (Brandel). The filter paper after filtration was washed three times with 1 mL of a solution containing 50 mmol/L HEPES-NaOH (pH 7.4), 500 mmol/L NaCl, and 0.1% BSA. The GF/C filter paper was put into an assay vial and 5 mL of a liquid scintillator, Atomlight, was added thereto. The radioactive activity was measured using a liquid scintillation counter (Perkin Elmer). The measurement was carried out once in duplicate in all cases. The specific binding amount was determined by subtracting the non-specific binding amount from the total binding amount. The Ki value was calculated according to a standard method.

As a result of the evaluation, it was found that the Ki value of Compound A with respect to the human EP4 receptor was 1.46 nmol/L.

Test Example 3: Evaluation Test of Human EP4 Receptor Antagonistic Action by Measurement of cAMP Amount in Human Jurkat Cells Cell Culture:
Jurkat cells (derived from human leukemia T lymphoma) were cultured under the conditions of 37° C. and 5% CO$_2$, using an RPMI1640 culture medium (product No. 11879020, Invitrogen Inc.) with 10% fetal bovine serum (FBS) added. After proliferation up to semiconfluency, indomethacin having a final concentration of 5 mol/L was added thereto, and the cells were further cultured for 18 hours. These cells were collected in a 15 mL Spitz tube, prepared at $1\times10^6$ cells/mL using a Cell Banker (Mitsubishi Kagaku Iatron), and stored at −80° C.

Treatment with Compound:

A test compound was prepared by dilution with an assay buffer containing 0.5% BSA (1×HBSS (Hanks buffered salt solution, Nissui Pharmaceutical Co., Ltd.), 20 mmol/L HEPES-NaOH (Nakalai Tesque Inc.) (pH 7.4), 0.5 mmol/L IBMX (3-isobutyl-1-methylxanthine, WAKO), 0.02% CHAPS (Sigma), 0.5% BSA (Sigma), and 2 μmol/L indomethacin (Sigma)) to be adjusted to a 3-fold concentration relative to the final concentration. PGE2 was prepared at 300 nmol/L with an assay buffer containing 0.5% BSA. The Jurkat cells cryopreserved were prepared at $1\times10^6$ cells/mL by thawing them at 37° C. using an assay buffer containing 0.5% BSA. To a 384-well U-bottom black microplate (Corning) were added the test compounds (final concentrations of 0.01, 0.03, 0.1, 0.3, 1, 3, and 10 nmol/L), the cells, and PGE2 in this order each in an amount of 5 μL, followed by shaking with a plate shaker and then incubating at room temperature for 30 minutes. In order to determine the amount of the cAMP in the state of PGE2 non-stimulation, a non-PGE2-added group was provided.

Measurement and Analysis of cAMP Amount:

A cAMP HiRange kit (Cisbio international) was used for cAMP measurement. After incubation, 5 μL of a d2 reagent which had been diluted 0.6-fold with a lysis buffer (50 mmol/L phosphate buffer (pH 7.0), 0.8 mol/L KF, 1% TritonX-100, 0.2% BSA) was added to each well, followed by shaking with a plate shaker. Subsequently, 5 μL of a europium cryptate reagent of a kit which had been diluted 0.6-fold with a lysis buffer was added to each well, followed by shaking with a plate shaker and incubating at room temperature for 60 minutes with light shielding. After incubation, the fluorescence intensity of the cryptate at 620 nm and the fluorescence intensity of the d2 at 665 nm were measured using ARVO1420 (PerkinElmer). The cAMPs at 280, 70, 17.5, 4.38, 1.09, 0.27, and 0.068 nmol/L were added to each well and the fluorescence intensity was measured as described above to create a standard curve. All measurements were performed in triplicate. The $IC_{50}$ values by the compound were calculated by a Logistic regression method, from the cAMP amount with a treatment with the compound, by taking the cAMP amount with addition of PGE2 as 100% and taking the cAMP amount without addition of PGE2 as 0%. An average value was calculated from three experiment results.

As a result of the evaluation, it was found that the $IC_{50}$ value with respect to the cAMP production action by PGE2 (100 nmol/L) of Compound A in human Jurkat cells was 0.16 nmol/L.

Test Example 4: Evaluation Test of Rat EP4 Receptor Antagonistic Action by Measurement of cAMP Amount Construction of Vector Expressing Rat EP4 Receptor:

The construction was carried out in the same manner as in Test Example 1.

Construction of Cells Stably Expressing Rat EP4 Receptor:

The expression vector of a rat EP4 receptor was transfected into a CHO—K1 cell (ATCC No.: CCL-61). The transfection was carried out according to an appended instruction, using Lipofectoamine (registered trademark) 2000 reagent (Invitrogen Inc.). After the transfection, the cells were cultured in an α-MEM culture medium (product No. 12571063, Invitrogen Inc.) containing G418 (Nakalai Tesque Inc.) to acquire a drug-resistant clone.

Cell Culture and Treatment with Compound:

CHO—K1 cells stably expressing a rat EP4 were seeded in 96-well plates at $0.5\times10^4$ cells/100 μL and cultured overnight. The culture medium was replaced with 2 μmol/L indomethacin/0.5% BSA/α-MEM culture medium, and further, after 60 minutes, replaced with 1 mmol/L IBMX/2 μmol/L indomethacin/0.5% BSA/α-MEM culture medium. After 10 minutes, the test compounds (final concentration of 0.1, 0.3, 1, 3, and 10 nmol/L) were added, and further, after 10 minutes, PGE2 was added to a final concentration of 100 nmol/L (final DMSO concentration of 0.1%). In order to calculate the amount of cAMP by the addition of PGE2, a group without addition of PGE2 was provided. The cells were cultured and reacted in a $CO_2$ incubator (37° C., 5% $CO_2$). After 30 minutes, the culture medium was removed and 100 μL/well of 0.2% Triton X-PBS was added for lysis of the cells. The test was carried out in duplicate twice.

Measurement and Analysis of cAMP Amount:

The cAMP amount in the cell lysate was measured using a cAMP HiRange kit. The cell lysate in each well was distributed to a 384-well U-bottom black microplate in an amount of 10 μL, 5 μL of each of a d2 reagent and a europium cryptate reagent were added thereto in this order, followed by incubating at room temperature for 60 minutes with light shielding. After incubation, the fluorescence intensity of the cryptate at 620 nm and the fluorescence intensity of the d2 at 665 nm were measured using ARVO1420. The cAMPs of 280, 70, 17.5, 4.38, 1.09, 0.27, and 0.068 nmol/L were added to each well to create a standard curve and the fluorescence intensity was measured as described above. The $IC_{50}$ values of the test compounds were calculated by a Logistic regression method from the cAMP amount with a treatment with the test compound, by taking the cAMP amount with addition of PGE2 having a final concentration of 100 nmol/L as 100% and taking the cAMP amount without addition of PGE2 as 0%. An average value was calculated from two experiment results.

As a result of the evaluation, it was found that the $IC_{50}$ value with respect to the cAMP production action by PGE2 (100 nmol/L) of Compound A in rat EP4 receptor expressing CHO—K1 cells was 1.04 nmol/L.

Test Example 5: Evaluation Test of In Vivo Rat EP4 Receptor Antagonistic Action

SD rats (male, 6-week old) under non-fasting conditions were used for the test. A test compound dissolved in a mixed solution of PEG 400: 20% Tween 80: 1 mol/L aqueous $NaHCO_3$ solution=1:4:5 was orally administered (po) to the rat at a dose of 0.03 mg/kg (5 mL/kg). After 1 hour, an active metabolite (ONO-AE1-437 (CAS No. 256382-23-7)) of an EP4 agonist ONO-4819 dissolved in physiological saline was subcutaneously administered (sc) to the back of the rat at a dose of 0.01 mg/kg (5 mL/kg). After 30 minutes, Lipopolysaccharide (LPS, 0.01 mg/kg) was administered to the tail vein (2 mL/kg), and after 60 minutes, about 0.5 mL of blood was collected in a heparin-containing tube under anesthesia. The blood sample was centrifuged (1000×g, 10 minutes, 4° C.) to separate the plasma. The TNF-α concentration in the rat plasma was measured by an ELISA kit (DuoSet ELISA, R&D Systems). An inhibitory rate of the test compound group (n=5) with respect to the TNF-α production inhibitory action by the EP4 agonist was calculated by taking the TNF-α concentration of the group (n=5) not treated with ONO-AE1-437 as 100% and taking the TNF-α concentration of the group (n=5) treated with ONO-AE1-437 as 0%.

As a result of the evaluation, it was found that Compound A (0.03 mg/kg, po) inhibited the TNF-α production inhibitory rate of the EP4 agonist ONO-AE1-437 (0.01 mg/kg, sc) by 38%.

Test Example 6: Evaluation Test of Action on Renin Activity in Rat Plasma

SD rats (male, 7-week old) under non-fasting conditions were used for the test. A test compound dissolved in a mixed solution of PEG 400:20% Tween 80:1 mol/L aqueous $NaHCO_3$ solution=1:4:5 was orally administered (po) to the rat at a dose of 0.3 mg/kg (5 mL/kg). After 1 hour, an active metabolite (ONO-AE1-437) of an EP4 agonist ONO-4819 dissolved in physiological saline was subcutaneously administered to the back of the rat at a dose of 0.01 mg/kg (5 mL/kg). After 10 minutes, the rat was decapitated without anesthesia and about 2 mL of blood was collected in a tube containing 3 mg of EDTA.2Na. The blood sample was centrifuged (1000×g, 10 minutes, 4° C.) to separate the plasma. To 100 μL of the plasma were added 10 μL of an assay buffer (20.4 mL of 2 mol/L $NaH_2PO_4$, 9.3 mL of 1 mol/L $Na_2HPO_4$, 15 mL of 0.5 mol/L EDTA.2Na, and 0.1 g of CHAPS were mixed, followed by mixing with distilled water and diluting to 50 mL, pH 5.55) and 1 μL of 100 mmol/L 4-(2-aminoethyl)benzenesulfonyl fluoride hydrochloride. A half of the amount was collected, followed by incubating at 37° C. for 90 minutes. The other half of the amount was stored at 4° C. and used for a blank reaction. The Angiotensin I concentration in both samples was measured by an ELISA method, and a concentration obtained by subtracting a value of the blank reaction from the value of the sample incubated at 37° C. was taken as a renin activity in plasma (plasma renin activity (PRA)). By taking the PRA of the inhibitor rate of the group (n=5) not treated with ONO-AE1-437 as 100% and taking that of the group (n=4) treated with ONO-AE1-437 as 0%, the inhibitory rate of the test compound group (n=5) was calculated.

As a result of the evaluation, it was found that Compound A (0.3 mg/kg, po) inhibited the increase in PRA due to the EP4 agonist ONO-AE1-437 (0.01 mg/kg, sc) by 102%.

Test Example 7: Test for Investigation of Effect on Albumin in Urine of db/db Mice with Type 2 Diabetes db/db Mice (male, 8-week old) with type 2 diabetes were used for the test. The albumin concentrations in urine samples obtained by urine collection for 24 hours were measured by an ELISA method using an anti-mouse albumin antibody (RAM/Alb/7S, Nordic Immunology), and the creatinine concentration in urine was measured using CRE-EN Kainos (Kainos Co., Ltd.). The albumin-creatinine ratio (ACR) in urine was calculated, and a group (n=12) not treated with the test compound and a group (n=12) treated with the test compound were allocated without a bias in ACR. The test compound suspended in a 0.5% methyl cellulose (MC) solution was orally administered to the group treated with the test compound at a dose of 0.3 mg/kg once per day for one week (10 mL/kg). A 0.5% MC solution was orally administered to the group not treated with the test compound at an administration volume of 10 mL/kg once per day for one week. Urine was collected for 24 hours from the completion of the final administration, and using the calculated ACR as an indicator, the improvement effect of the test compound on the early nephropathy of the mice with type 2 diabetes was investigated. The inhibitory rate of ACR of the group treated with the test compound by taking the ACR value of the group not treated with the test compound as 100% was determined.

As a result of the evaluation, it was found that Compound A (0.3 mg/kg, po) inhibited the ACR of the db/db mouse with type 2 diabetes by 44% by oral administration for one week.

Test Example 8: Test for Investigation of Effect on Renal Function of 5/6 Nephrectomy (5/6 Nx) of Rats with Chronic Renal Failure Wistar rats (male, 8-Week-old) were used for the test. Two-thirds of the left kidney was removed under pentobarbital anesthesia, and after 1 week, the entire right kidney was nephrectomized (5/6 Nx). After 2 weeks from 5/6 Nx, the protein concentrations in urine samples obtained by urine collection for 24 hours were measured using a Bio-Rad Protein assay kit, and the creatinine concentration in urine was measured using Determiner L CRE (Kyowa Medex Co., Ltd.)). The urinary protein-creatinine ratio (UPCR) was calculated, and a group (n=12) not treated with the test compound and a group (n=12) treated with the test compound were allocated without a bias in UPCR. The test compound suspended in a 0.5% MC solution was orally administered to the group treated with the test compound at a dose of 0.2 mg/kg once per day for 6 weeks (5 mL/kg). A 0.5% MC solution was orally administered to the group not treated with the test compound at an administration volume of 5 mL/kg once per day for 6 weeks. Urine was collected for 24 hours from the completion of the final administration, and using the calculated UPCR as an indicator, the improvement effect of the test compound on the nephropathy of the rat with chronic renal failure was investigated. The inhibitory rate of UPCR of the group treated with the test compound when the UPCR value of the group not treated with the test compound was taken as 100% was determined.

As a result of the evaluation, Compound A (0.2 mg/kg, po) inhibited the UPCR of the rat with 5/6 nephrectomy chronic renal failure by 47% by oral administration for 6 weeks.

Test Example 9: Evaluation Test of Receptor Antagonistic Action on Rat EP1/EP2/EP3 Receptor (Selectivity Test)

The antagonistic action of Compound A on other subtypes (EP, EP2, and EP3) of the rat-derived PGE2 receptor was evaluated. For EP1 and EP3, the intracellular $Ca^{2+}$ amount was used as an indicator, and for EP2, the intracellular cAMP amount was used as an indicator, so as to investigate the action of the test compound.

Construction of Rat EP1, EP2, or EP3 Receptor Expressing Vector: A rat EP1 receptor gene (GenBank accession No.: D88751.1), a rat EP2 receptor gene (GenBank accession No.: NM_031088.1), or a rat EP3 receptor gene (GenBank accession No.: NM_012704.1) were inserted respectively into an expression vector pcDNA3.1-V5-His-TOPO (Invitrogen Inc.).

Construction of Cell Stably Expressing Rat EP1, EP2, or EP3 Receptor:

The vector expressing a rat EP1, EP2, or EP3 receptor was transfected into an HEK-293 cell (for stably expressing a rat EP1 or EP3 receptor, ATCC No.: CRL-1573) or a CHO—K1 cell (for stably expressing a rat EP2 receptor, ATCC No.: CCL-61). The transfection was carried out according to an appended instruction, using Lipofectoamine (registered trademark) 2000 reagent (Invitrogen Inc.). After the transfection, the cells were cultured in a D-MEM culture medium (for stably expressing a rat EP1 or EP3 receptor) (product No. 11885084, Invitrogen Inc.) containing G418 (Nakalai Tesque Inc.) and an α-MEM culture medium (for stably expressing a rat EP2 receptor) containing G418 to acquire a drug-resistant clone.

Culture of Cell Stably Expressing EP2 Receptor and Treatment with Compound:

CHO—K1 cells stably expressing rat EP2 were seeded in 96-well plates at $1 \times 10^4$ cells/100 μL and cultured overnight under the conditions of 37° C. and 5% $CO_2$, using an α-MEM culture medium having 10% FBS added thereto. The culture medium was replaced with 2 kmol/L indomethacin/0.1% BSA/α-MEM culture medium, and further, after 60 minutes, replaced with 1 mmol/L IBMX/2 μmol/L indomethacin/0.1% BSA/α-MEM culture medium (product No. 12571063, Invitrogen Inc.). After 10 minutes, the test compounds (final concentration of 0.01, 0.1, 1, and 10 μmol/L) were added, and further, after 10 minutes, PGE2 was added to a final concentration of 100 nmol/L (final DMSO concentration of 0.1%). In order to calculate the amount of cAMP produced by the addition of PGE2, a group without addition of PGE2 was provided. The cells were cultured and reacted in a $CO_2$ incubator (37° C., 5% $CO_2$). After 30 minutes, the culture medium was removed and 100 μL/well of 0.2% Triton X-PBS was added for lysis of the cells. The test was carried out once in duplicate.

Measurement and Analysis of cAMP Amount in Cell Stably Expressing EP2 Receptor:

The amount of cAMP contained in the cell lysate was measured with a cAMP HiRange kit in the same manner as in Test Example 4. The ratio of the cAMP amount when the test compound was treated was calculated, by taking the cAMP amount with addition of PGE2 having a final concentration of 100 nmol/L as 100% and taking the cAMP amount without addition of PGE2 as 0%.

As a result of the evaluation, Compound A did not exhibit an inhibitory action of 50% or more to 10,000 nmol/L with respect to the increase in the cAMP amount in the cell due to PGE2 through the rat EP2 receptor.

Culture of Cells Stably Expressing EP1 and EP3 Receptors and Treatment with Compound:

An HEK-293 cell stably expressing rat EP1 or rat EP3 was seeded in 96-well plates at $1 \times 10^4$ cells/100 μL and cultured overnight under the conditions of 37° C. and 5% $CO_2$, using a D-MEM culture medium having 10% FBS added thereto. To an assay buffer (1×HBSS, 20 mmol/L HEPES-NaOH (pH 7.4), 0.6 mg/mL probenecid, 0.1% BSA) was added a fluorescent reagent Dye of Ca3 Assay kit (Molecular Devices, LLC.) at a ratio of 70:1. The culture medium was replaced with the diluted Dye solution, followed by incubating for 3 hours. The compound (final concentration of 1 or 10 μmol/L) dissolved in DMSO and the assay buffer was added thereto. After 5 minutes, PGE2 was added to a final concentration of 100 nmol/L (final DMSO concentration of 1%). The test using a cell stably expressing a rat EP1 receptor or a rat EP3 receptor was carried out once in duplicate.

Measurement and Analysis of $Ca^{2+}$ Concentration in Cell Stably Expressing EP1 or EP3 Receptor:

The intracellular $Ca^{2+}$ concentration was measured using FLIPR tetra (Molecular Devices, LLC.) with the fluorescence intensity of the Dye as an indicator. In order to measure the intracellular $Ca^{2+}$ concentration by the addition of PGE2, a non-PGE2-added group was provided. By taking the $Ca^{2+}$ concentration when PGE2 was added to a final concentration of 100 nmol/L as 100%, and taking the $Ca^{2+}$ concentration when PGE2 was not added as 0%, the $Ca^{2+}$ concentration in percentage with a treatment with the compound was calculated.

As a result of the evaluation, Compound A did not exhibit an inhibitory action of 50% or more to 10,000 nmol/L with respect to the increase in the intracellular $Ca^{2+}$ concentration due to PGE2 through the EP1 or EP3 receptor of the rat.

Test Example 10: Evaluation on Rat Gastrointestinal Disorder

SD rats (male, 7-week old) were used. A test compound dissolved in a mixed solution of PEG 400: 20% Tween 80: 1 mol/L aqueous $NaHCO_3$ solution=1:4:5 was orally administered at a dose of 3 mg/kg (n=5, 5 mL/kg) for 7 days. The aforementioned mixed liquid was orally administered to a group not treated with the test drug (n=5) at a volume of 5 mL/kg for 7 days. Blood was collected under fasting overnight for hematology and blood chemistry tests on the following day after the final administration. After blood collection, the animal which had been euthanized by exsanguination was immediately necropsied, and the stomach, duodenum, jejunum, ileum, cecum, colon, rectum, and liver were excised therefrom. The excised organs were fixed in a 10% neutral buffered formalin solution and used for histopathological evaluation.

The results of the evaluation, findings indicating that Compound A caused abnormality were not observed.

As a result of the test, it was confirmed that Compound A has an EP4 receptor affinity and exhibits an excellent EP4 receptor antagonistic action (Test Examples 1 to 5). It was confirmed that Compound A inhibits the increase in the PRA caused by the EP4 agonist (Test Example 6). It was confirmed that Compound A has improvement effects in test for investigation of effect on albumin in urine of db/db mice with Type 2 Diabetes and test for investigation of effect on renal function of 5/6 nephrectomy (5/6 Nx) of rats with chronic renal failure (Test Examples 7 and 8).

Accordingly, Compound A or a salt thereof can be used for prevention or treatment for chronic renal failure and/or diabetic nephropathy.

From the results of Test Example 1 above, it was found that Compound A has an excellent EP4 receptor affinity, as compared with Example 205 in Patent Document 1. Further, from the results of Test Example 10 above, it was found that there is little concern for Compound A causing gastrointestinal disorders.

From the results of the tests above, it was confirmed that Compound A or a salt thereof has an EP4 receptor antagonistic action, and can be used as an active ingredient of a pharmaceutical composition for preventing or treating various EP4-related diseases, and the like. Examples of the EP4-related diseases include renal diseases (for example, renal sclerosis, gouty kidney, polycystic kidney disease, nephrotic syndrome, acute nephritis, recurrent hematuria, persistent hematuria, chronic nephritis, rapidly progressive nephritis, acute renal failure, chronic renal failure, diabetic nephropathy, and Bartter's syndrome), inflammatory skin diseases (for example, sunburn, burns, eczema, and dermatitis), ischemic heart diseases caused by arteriosclerosis (for example, myocardial infarction and angina), cerebrovascular disorders caused by arteriosclerosis (for example, stroke, stroke including lacunar infarction, cerebral thrombosis, cerebral hemorrhage, subarachnoid hemorrhage, and cerebral infarction), peptic ulcer diseases (for example, gastric ulcer and duodenal ulcer), malignant cancer and metastasis thereof (for example, colon cancer and breast cancer), pain (for example post-operative acute pain, traumatic pain, pain after stitches are removed, pain of the neck, shoulders and wrists, shoulder periarthritis, osteoarthritis (OA), carpal tunnel syndrome, rheumatoid arthritis (RA), postoperative chronic pain, interstitial cystitis, bladder pain syndrome, non-bacterial chronic prostatitis (CP/CPPS), pain after spinal cord injury, pain after cerebral infarction, multiple sclerosis (pain), pain of Parkinson's disease, diabetic neuropathic pain, postherpetic pain, HIV neuropathic pain, trigeminal neuralgia, fibromyalgia, low back pain (nociceptive, general low back pain including neuropathic low back pain), lumbar spinal canal stenosis, pain of spinal disorder (except for lumbar spine tube stenosis and spinal cord injury), thalamic pain, migraine, headache, restless legs (itching foot) syndrome, cancer pain, and irritable bowel syndrome), in particular, renal diseases such as chronic renal failure and/or diabetic nephropathy.

Further, Compound A or a salt thereof can be used as an agent for treating and/or preventing various types of edema (for example, cardiac edema and cerebral edema), hypertension such as malignant hypertension, premenstrual syndrome, urinary calculi, a urine depletion diseases as caused by an acute or chronic disease, hyperphosphatemia, or the like.

In addition, Compound A or a salt thereof can be used as an agent for treating and/or preventing various types of polyuria (for example, central diabetes insipidus, nephrogenic diabetes insipidus, psychogenic diabetes insipidus, diabetes mellitus, sodium chloride absorption disorders, and polydipsia).

A pharmaceutical composition containing Compound A or a salt thereof as an active ingredient can be prepared in accordance with a generally used method, using an excipient usually used in the art, that is, a pharmaceutical excipient, a pharmaceutical carrier, or the like.

The administration can be carried out in any form of oral administration via tablets, pills, capsules, granules, powders, liquid preparations, or the like; or parenteral administration via injections such as intraarticular, intravenous, or intramuscular injections, suppositories, eye drops, eye ointments, percutaneous liquid preparations, ointments, percutaneous patches, transmucosal liquid preparations, transmucosal patches, and inhalers.

As the solid composition for oral administration, tablets, powder, granules, or the like are used. In such a solid composition, one or more kinds of active ingredient are mixed with at least one inert excipient. According to a conventional method, the composition may contain inert additives such as a lubricant, a disintegrator, a stabilizing agent, and a solubilizing agent. As occasion demands, the tablets or the pills may be coated with a sugar coating, or a film of a gastric or enteric material.

The liquid composition for oral administration includes pharmaceutically acceptable emulsions, solutions, suspensions, syrups, elixirs, or the like, and contains a generally used inert diluent such as purified water or ethanol. In addition to the inert diluent, this liquid composition may contain an auxiliary agent such as a solubilizing agent, a moistening agent, and a suspending agent, a sweetener, a flavor, an aroma, and an antiseptic.

The injections for parenteral administration include sterile aqueous or non-aqueous liquid preparations, suspensions and emulsions. The aqueous solvent includes, for example, distilled water for injection and physiological saline. Examples of the non-aqueous solvent include alcohols such as ethanol. Such a composition may further contain a tonicity agent, an antiseptic, a moistening agent, an emulsifying agent, a dispersing agent, a stabilizing agent, or a solubilizing agent. These are sterilized, for example, by filtration through a bacteria-retaining filter, incorporation of a bactericide, or irradiation. Additionally, these can also be used by preparing a sterile solid composition, and dissolving or suspending it in sterile water or a sterile solvent for injection prior to its use.

Examples of the agent for external use includes ointments, plasters, creams, jellies, cataplasms, sprays, lotions, eye drops, eye ointments, and the like. The agents contain generally used ointment bases, lotion bases, aqueous or non-aqueous liquid preparations, suspensions, emulsions, or the like.

As the transmucosal agents such as an inhaler, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate propellant, for example, a suitable gas such as a chlorofluoroalkane and carbon dioxide, or other forms.

In oral administration, the daily dose is preferably from about 0.001 to 100 mg/kg, in an embodiment, from 0.1 to 30 mg/kg, and in another embodiment, from 0.1 to 10 mg/kg, per body weight, administered in one portion or in 2 to 4 separate portions. In the case of intravenous administration, the daily dose is suitably from about 0.0001 to 10 mg/kg per body weight, once a day or two or more times a day. Additionally, a transmucosal agent is administered at a dose in a range from about 0.001 to 100 mg/kg per body weight, once a day or two or more times a day. The dose is appropriately decided in response to individual cases by taking the symptoms, the age, and the gender, and the like into consideration.

Although it varies depending on the administration route, dosage form, administration site, the kinds of excipient and additive, the pharmaceutical composition of the present invention includes 0.01 by weight to 100% by weight, in an embodiment, 0.01 by weight to 50% by weight, of one or more kinds of Compound A as an active ingredient.

Compound A can be used in combination with various agents for treating or agents for preventing the above-described diseases for which Compound A is considered to be effective. The preparations to be used at the same time may be administered simultaneously, or separately and continuously or at a desired time interval. The preparations to be co-administered may be a blend, or may be prepared individually.

EXAMPLES

The preparation methods of Compound A represented by the formula (I) or a salt thereof will be described below in more detail based on Examples. The preparation methods for Compound A or a salt thereof are not limited only to the preparation methods (processes) of the specific Examples shown below, and Compound A or a salt thereof can be prepared by any methods that are apparent to a person skilled in the art.

In addition, the DSC analysis and the powder X-ray diffraction were carried out by the following methods.

(1) DSC Analysis

The DSC analysis was carried out using Q1000 and Q2000, manufactured by TA Instruments. Approximately 2 mg of a sample was filled into an aluminum sample pan dedicated for this use, and the difference in calories generated between a sample and a reference (empty aluminum sample pan) was continuously measured and recorded with a measurement range set from room temperature to 300° C. and a heating rate of 10° C./min in a state that the sample pan was not capped, under a nitrogen atmosphere (50 mL/min). Further, the handling with a device including a data processing was in accordance with the method and procedures instructed for each device.

(2) Powder X-Ray Diffraction

The powder X-ray diffraction was measured using a RINT-TTRII under the conditions of a tube: Cu, a tube current: 300 mA, a tube voltage, 50 kV, a sampling width: 0.020°, a scanning speed: 4°/min, a wavelength: 1.54056 angstroms, and a measurement diffraction angle (2θ): 2.5 to 40°. Further, the handling with a device including a data processing was in accordance with the method and procedures as indicated in each device.

Furthermore, in Examples the following abbreviations are used. ESI+: m/z values in ESI-MASS, NMR-DMSO-$d_6$: peak δ (ppm) in $^1$H NMR in DMSO-$d_6$.

In addition, for convenience, a concentration in mol/L is represented by M. For example, a 1 M aqueous sodium hydroxide solution means a 1 mol/L aqueous sodium hydroxide solution.

Example 1

Synthesis of 4-[(1S)-1-({[4-bromo-1-(isoquinolin-3-ylmethyl)-3-methyl-1H-pyrazol-5-yl]carbonyl}amino)ethyl]benzoic acid (I)

Step 1. Synthesis of methyl 4-[(1S)-1-{[(4-bromo-3-methyl-1H-pyrazol-5-yl)carbonyl]amino}ethyl]benzoate (5a)

[Chem. 13]

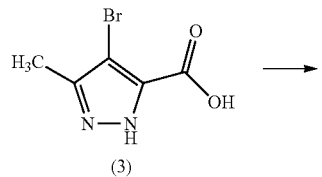

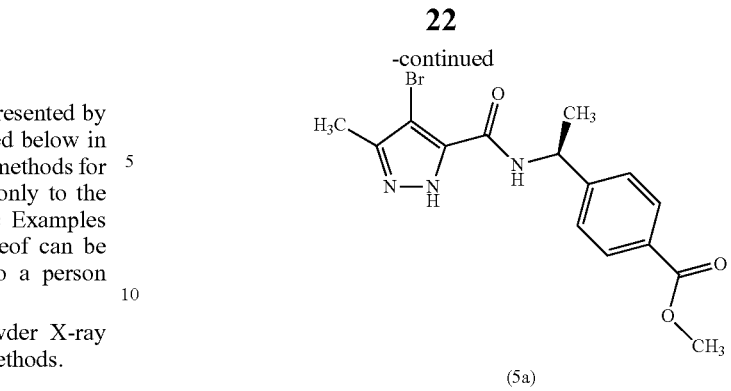

To a mixture of 4-bromo-3-methyl-1H-pyrazole-5-carboxylic acid (3) (1.00 g), DMF (20 mL), methyl 4-[(1S)-1-amino ethyl]benzoate hydrochloride (1.26 g), and HOBt (0.99 g) was added 1-(3-dimethylaminopropyl)-3-ethylcarbodiimide (1.2 mL), followed by stirring at room temperature overnight. To the mixture was added ethyl acetate, followed by stirring under ice-cooling. To the mixture was added a 10% aqueous citric acid solution, followed by separating into an organic layer and an aqueous layer, and the aqueous layer was extracted with ethyl acetate. The obtained organic layers were combined, sequentially washed with a saturated sodium hydrogen carbonate solution, water, and saturated brine, dried over anhydrous magnesium sulfate, and then filtered. The filtrate was concentrated under reduced pressure to obtain methyl 4-[(1S)-1-{[(4-bromo-3-methyl-1H-pyrazol-5-yl)carbonyl]amino}ethyl]benzoate (5a) (1.75 g).

ESI+: 366, 368

Step 2. Synthesis of methyl 4-[(1S)-1-({[4-bromo-1-(isoquinolin-3-ylmethyl)-3-methyl-1H-pyrazol-5-yl]carbonyl}amino)ethyl]benzoate (2a)

[Chem. 14]

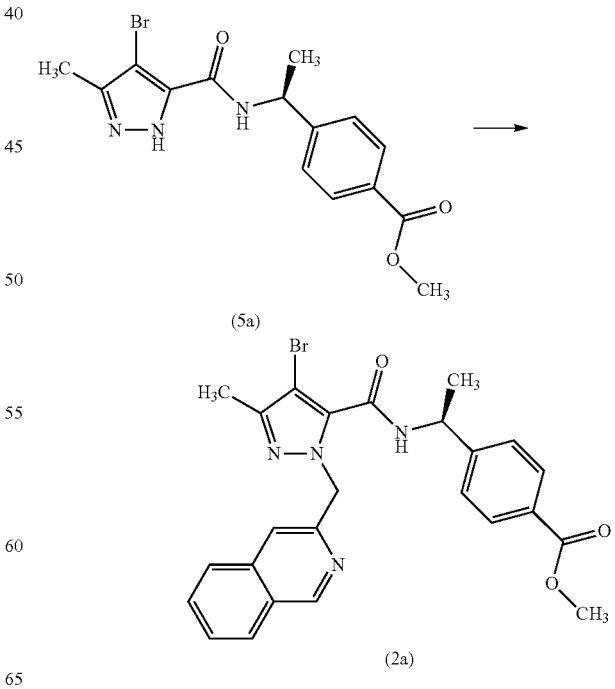

A mixture of methyl 4-[(1S)-1-{[(4-bromo-3-methyl-1H-pyrazol-5-yl)carbonyl]amino}ethyl]benzoate (5a) (1.72 g)

and DMF (20.0 mL) was stirred under ice-cooling. To the mixture was added potassium tert-butoxide (580 mg), followed by stirring for 0.5 hours. To the mixture was added a mixture of 3-(bromomethyl)isoquinoline (1.10 g) and DMF (14 mL), followed by warming to room temperature and stirring for 10 days. The obtained mixture was stirred under ice-cooling, and ethyl acetate and a 10% aqueous citric acid solution were added thereto, followed by stirring for a while and extracting with ethyl acetate. The obtained organic layer was sequentially washed with a saturated aqueous sodium hydrogen carbonate solution, water, and saturated brine, dried over anhydrous magnesium sulfate, and then filtered. The filtrate was concentrated under reduced pressure, and the residue was purified by silica gel column chromatography (normal hexane:ethyl acetate=6:4) to obtain methyl 4-[(1S)-1-({[4-bromo-1-(isoquinolin-3-ylmethyl)-3-methyl-1H-pyrazol-5-yl]carbonyl}amino)ethyl]benzoate (2a) (518 mg).

NMR-DMSO-$d_6$: 9.28 (1H, d, J=7.8 Hz), 9.23 (1H, s), 8.13 (1H, d, J=7.8 Hz), 7.89 (1H, d, J=7.8 Hz), 7.81-7.76 (1H, m), 7.72-7.64 (3H, m), 7.50 (1H, s), 7.38 (2H, d, J=8.3 Hz), 5.65-5.54 (2H, m), 5.12-5.04 (1H, m), 3.83 (3H, s), 2.17 (3H, s), 1.37 (3H, d, J=7.0 Hz)

Step 3. Synthesis of 4-[(1S)-1-({[4-bromo-1-(isoquinolin-3-ylmethyl)-3-methyl-1H-pyrazol-5-yl]carbonyl}amino)ethyl]benzoic acid (I)

[Chem. 15]

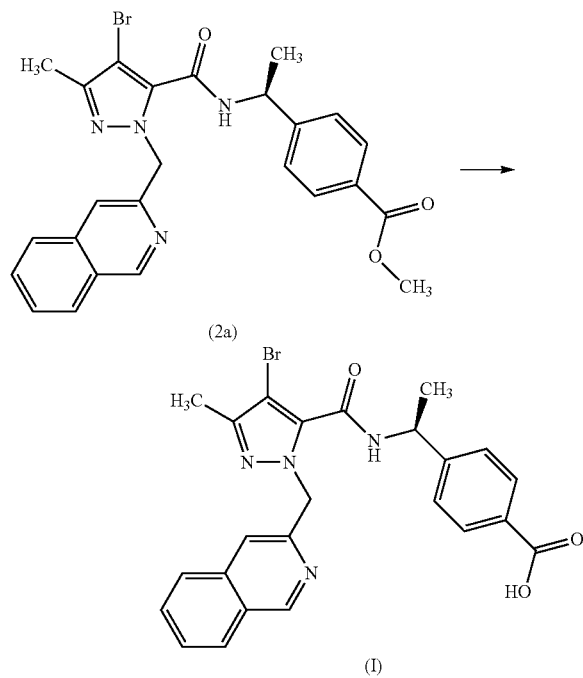

To a mixture of methyl 4-[(1S)-1-({[4-bromo-1-(isoquinolin-3-ylmethyl)-3-methyl-1H-pyrazol-5-yl]carbonyl}amino)ethyl]benzoate (2a) (486 mg), THF (10.0 mL), and methanol (10.0 mL) was added a 2 M aqueous sodium hydroxide solution (5.0 mL) under ice-cooling, followed by stirring at room temperature for 17 hours. To the mixture was added 1 M hydrochloric acid (10.0 mL) under ice-cooling, followed by warming to room temperature and stirring for 2 hours. The precipitated solid was collected by filtration and washed with water to obtain 4-[(1S)-1-({[4-bromo-1-(isoquinolin-3-ylmethyl)-3-methyl-1H-pyrazol-5-yl]carbonyl}amino)ethyl]benzoic acid (I) (411 mg) as crystals.

ESI+: 493, 495

NMR-DMSO-$d_6$: 12.9-12.7 (1H, m), 9.30 (1H, d, J=7.8 Hz), 9.24 (1H, s), 8.13 (1H, d, J=8.1 Hz), 7.91 (1H, d, J=8.1 Hz), 7.81-7.76 (1H, m), 7.74-7.66 (3H, m), 7.53 (1H, s), 7.40 (2H, d, J=8.2 Hz), 5.60 (2H, s), 5.14-5.03 (1H, m), 2.16 (3H, s), 1.37 (3H, d, J=7.0 Hz)

Elemental analysis: Calcd. for $C_{24}H_{21}BrN_4O_3$: C, 58.43; H, 4.29; N, 11.36; Br, 16.20.

Found: C, 58.33; H, 4.38; N, 11.24; Br, 16.07.

As a result obtained by subjecting the crystals obtained in Step 3 of Example 1 to powder X-ray diffraction measurement using Cu as a tube, a chart including peaks at 2θ (°)=5.7, 7.9, 8.3, 8.9, 9.2, 11.5, 12.5, 13.1, 15.8, 16.3, 16.7, 17.2, 17.9, 18.5, and 19.5 was obtained.

As a result of the DSC analysis of the crystals obtained in Step 3 of Example 1, the onset temperature of an endothermic peak was 253° C.

Example 2

Synthesis of 4-[(1S)-1-({[4-bromo-1-(isoquinolin-3-ylmethyl)-3-methyl-1H-pyrazol-5-yl]carbonyl}amino)ethyl]benzoic acid methanesulfonate (Ia)

[Chem. 16]

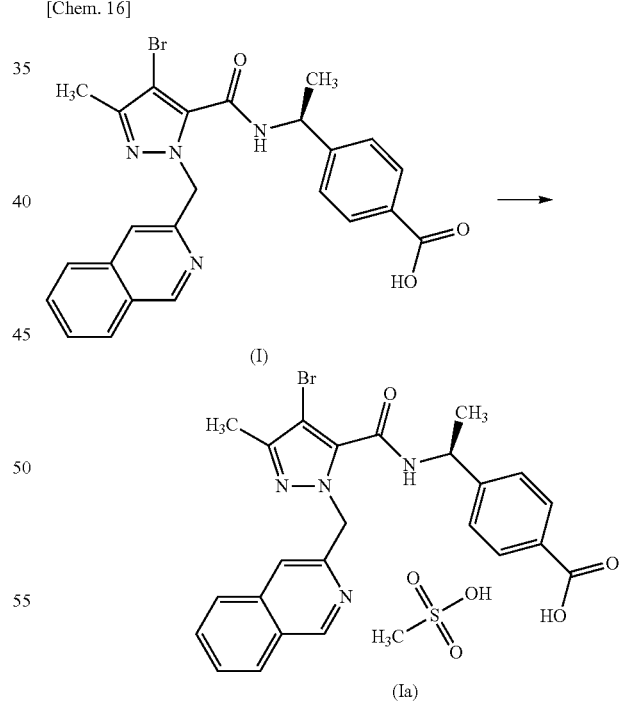

To a mixture of 4-[(1S)-1-({[4-bromo-1-(isoquinolin-3-ylmethyl)-3-methyl-1H-pyrazol-5-yl]carbonyl}amino)ethyl]benzoic acid (I) (1000.0 mg) and dioxane (30 mL) was added methanesulfonic acid (140 μL) under ice-cooling. The obtained mixture was warmed to 90° C. and stirred for 1 hour. After cooling to room temperature, the precipitated solid was collected by filtration to obtain 4-[(1S)-1-({[4- bromo-1-(isoquinolin-3-ylmethyl)-3-methyl-1H-pyrazol-5-yl]carbonyl}amino)ethyl]benzoic acid methanesulfonate (Ia) as crystals (1030 mg).

ESI+: 493, 495

NMR-DMSO-$d_6$: 9.32 (1H, s), 9.27 (1H, d, J=7.7 Hz), 8.17 (1H, d, J=7.9 Hz), 7.95 (1H, d, J=7.9 Hz), 7.90-7.79 (1H, m), 7.77-7.66 (3H, m), 7.59 (1H, s), 7.40 (2H, d, J=7.8 Hz), 5.71-5.54 (2H, m), 5.16-5.00 (1H, m), 2.33 (3H, s), 2.17 (3H, s), 1.37 (3H, d, J=7.1 Hz)

Elemental analysis: Calcd. for $C_{24}H_{21}BrN_4O_3 \cdot CH_4O_3S$: C, 50.94; H, 4.27; N, 9.50; S, 5.44; Br, 13.56.

Found: C, 50.65; H, 4.25; N, 9.36; S, 5.41; Br, 13.42.

As a result obtained by subjecting the crystals obtained in Example 2 to powder X-ray diffraction measurement using Cu as a tube, a chart including peaks at 2θ (°)=4.7, 9.5, 12.0, 13.2, 13.7, 15.3, 18.8, 20.3, 20.9, and 22.8 was obtained.

As a result of the DSC analysis of the crystals obtained in Example 2, the onset temperature of an endothermic peak was 192° C.

INDUSTRIAL APPLICABILITY

Compound A or a salt thereof has an EP4 receptor antagonistic action and can be used as an active ingredient of a pharmaceutical composition for preventing and/or treating chronic renal failure and/or diabetic nephropathy.

The invention claimed is:

1. A compound which is 4-[(1S)-1-({[4-Bromo-1-(isoquinolin-3-ylmethyl)-3-methyl-1H-pyrazol-5-yl]carbonyl}amino)ethyl]benzoic acid or a pharmaceutically acceptable salt thereof.

2. The compound or pharmaceutically acceptable salt according to claim 1, which is 4-[(1S)-1-({[4-bromo-1-(isoquinolin-3-ylmethyl)-3-methyl-1H-pyrazol-5-yl]carbonyl}amino)ethyl]benzoic acid methanesulfonate.

3. The compound or pharmaceutically acceptable salt according to claim 2, which is a crystal of 4-[(1S)-1-({[4-bromo-1-(isoquinolin-3-ylmethyl)-3-methyl-1H-pyrazol-5-yl]carbonyl}amino)ethyl]benzoic acid methanesulfonate.

4. The compound or pharmaceutically acceptable salt according to claim 3, which is a crystal having an onset temperature of an endothermic peak in DSC analysis of 192° C., and having peaks at 2θ (°)=4.7, 9.5, 12.0, 13.2, 13.7, 15.3, 18.8, 20.3, 20.9, and 22.8 in powder X-ray diffraction using Cu as a tube.

5. A pharmaceutical composition, comprising the compound or pharmaceutically acceptable salt salt thereof according to claim 1, and a pharmaceutically acceptable excipient.

6. A method for treating a disease or condition selected from the group consisting of chronic renal failure and diabetic nephropathy, said method comprising administering an effective amount of the compound or pharmaceutically acceptable salt thereof according to claim 1 to a subject in need thereof.

7. A pharmaceutical composition, comprising the crystal according to claim 3, and a pharmaceutically acceptable excipient.

8. A method for treating chronic renal failure, comprising administering an effective amount of the compound or pharmaceutically acceptable salt thereof according to claim 1 to a subject in need thereof.

9. A method for treating diabetic nephropathy, comprising administering an effective amount of the compound or pharmaceutically acceptable salt thereof according to claim 1 to a subject in need thereof.

* * * * *

UNITED STATES PATENT AND TRADEMARK OFFICE
CERTIFICATE OF CORRECTION

| | |
|---|---|
| PATENT NO. | : 10,106,523 B2 |
| APPLICATION NO. | : 15/127574 |
| DATED | : October 23, 2018 |
| INVENTOR(S) | : Takao Okuda et al. |

It is certified that error appears in the above-identified patent and that said Letters Patent is hereby corrected as shown below:

In Claim 5, Column 26, Line 14, (approx.):
"pharmaceutically acceptable salt salt thereof"
Should read:
--pharmaceutically acceptable salt thereof--

Signed and Sealed this
Eleventh Day of December, 2018

Andrei Iancu
*Director of the United States Patent and Trademark Office*